US00PP09617P

United States Patent [19]

Vlielander

[11] Patent Number: Plant 9,617

[45] Date of Patent: Jul. 30, 1996

[54] KALANCHOE PLANT NAMED TENORIO

[75] Inventor: Ike Vlielander, De Lier, Netherlands

[73] Assignee: Fides Beheer B.V., De Lier, Netherlands

[21] Appl. No.: 506,333

[22] Filed: Jul. 24, 1995

[51] Int. Cl.[6] ..... A01H 5/00

[52] U.S. Cl. ..... Plt./87.15

[58] Field of Search ..... Plt./87.15

*Primary Examiner*—James R. Feyrer
*Attorney, Agent, or Firm*—C. A. Whealy

[57] ABSTRACT

A distinct cultivar of Kalanchoe plant named Tenorio, characterized by its bright red flower color; moderately vigorous plant growth habit; freely branching habit; proportional leaf size to plant size; uniform inflorescence display; floriferousness; flowers that are tolerant to high water salinity levels; and good postproduction longevity.

1 Drawing Sheet

The present invention relates to a new and distinctive cultivar of Kalanchoe plant, botanically known as *Kalanchoe blossfeldiana,* and hereinafter referred to by the cultivar name Tenorio.

The new cultivar is a product of a planned breeding program conducted by the inventor in De Lier, Holland. The objective of the breeding program was to create a new Kalanchoe cultivar having a uniform plant habit, good flower and foliage colors, and flowers and foliage with good substance.

The new cultivar originated from a cross made by the inventor of the nonpatented cultivar Krakatau as the male or pollen parent with the proprietary selection FK 2670 as the female or seed parent.

The cultivar Tenorio was discovered and selected by the inventor as a flowering plant within the progeny of the stated cross in a controlled environment in De Lier, Holland. Asexual reproduction of the new cultivar by terminal cuttings taken at De Lier, Holland, has shown that the unique features of this new Kalanchoe are stabilized and reproduced true to type in successive generations.

The cultivar Tenorio has not been observed under all possible environmental conditions. The phenotype may vary somewhat with variations in environment such as temperature, daylength and light intensity, without, however, any variance in genotype. The following observations, measurements and comparisons describe plants grown in De Lier, Holland, under commercial practice in a glass-covered greenhouse.

The following traits have been repeatedly observed and are determined to be the unique characteristics of Tenorio. These characteristics in combination distinguish Tenorio as a new and distinct cultivar:

1. Bright red flower color.
2. Moderately vigorous plant growth habit.
3. Freely branching habit with shoots forming at every node. Plants do not require pinching.
4. Proportional leaf size to plant size.
5. Suitable for various container sizes from 10 to 15 cm.
6. Uniform inflorescence display.
7. Very floriferous with numerous flowers per plant.
8. Flowers are tolerant to high water salinity levels.
9. Good postproduction longevity. Flowers do not fade and foliage maintains good color and substance for at least six weeks under interior conditions.

The new Kalanchoe differs from its parents in the color of the petals. The petal colors of the male parent, Krakatau, and the female parent, selection FK 2670, are lighter red than petals of the cultivar Tenorio. Plants of the cultivar Krakatau have darker foliage, larger leaves, are more vigorous, and flowers are sensitive to high water salinity levels in comparison to plants of the cultivar Tenorio. Plants of the selection FK 2670 are more vigorous than plants of the cultivar Tenorio.

Tenorio is most similar to the nonpatented Kalanchoe cultivar Aroi. However Tenorio differs from Ario in the following characteristics:

1. Plants of Tenorio are more vigorous than plants of Aroi.
2. Leaves of Tenorio are narrower and shorter than leaves of Aroi.
3. Foliage color of Tenorio is lighter than foliage color of Aroi.
4. Flowers of plants of Tenorio are larger than flowers of plants of Aroi.
5. Petal color of Tenorio is darker red than petal color of Aroi.
6. Plants of Tenorio flower about one week later than plants of Aroi.
7. Flowers of plants of Tenorio are not sensitive to high water salinity levels, whereas flowers of plants of Aroi are sensitive to high water salinity levels.

The accompanying colored photograph illustrates the overall appearance of the new cultivar, showing the colors as true as it is reasonably possible to obtain in colored reproductions of this type. The photograph comprises a top perspective view of a typical potted plant of Tenorio taken under natural light conditions at approximately noon in De Lier, Holland.

In the following description, color references are made to The Royal Horticultural Society Colour Chart except where general terms of ordinary dictionary significance are used. Measurements and numerical values represent averages for twelve typical plants in 11-cm containers.

Botanical classifiction: *Kalanchoe blossfeldiana* cultivar Tenorio.

Parentage:

*Male.*—Nonpatented cultivar Krakatau.

*Female.*—Proprietary selection FK 2670.

Propagation:

A. *Type cutting.*—Terminal cuttings.

B. *Time to initiate roots.*—12 days at 21° C. soil temperature.

C. *Rooting habit.*—Numerous, fine, fibrous, and well-branched.

Plant description:

A. *Form.*—Upright and uniform.

B. *Habit of growth.*—Freely branching, generally shoots formed at every node.

C. *Plant height at flowering.*—18 cm.

D. *Vigor.*—Moderately vigorous.

E. *Foliage description.*—Leaves simple, opposite, generally symmetrical. 1. Size: a. Length: 11.5 cm. b. Width: 7.5 cm. 2. Shape: Elliptic. a. Apex: Acute to obtuse. b. Base: Acute. 3. Texture: Glabrous, coriaceous, succulent. 4. Margin: Crenate. 5. Color: a. Young foliage top side: 138A. b. Young foliage under side: 138B. c. Mature foliage top side: 138A. d. Mature foliage under side: 138B. e. Stem color: 138B.

Flower description:

A. *Flower type and habit.*—Flowers arranged in panicles, compound dichasial cymes on fairly strong peduncles. Freely flowering and very floriferous with new buds continuing to develop.

B. *Natural flowering season.*—Autumn/winter in Northern Hemisphere. Flower initiation and development can be induced under short day/long night conditions. Opening of new buds will continue for at least seven weeks. Individual flowers last at least two weeks after opening.

C. *Inflorescences borne.*—Above foliage, arising from leaf axils. Inflorescence of each shoot is formed by dichotomous branching.

D. *Time to flower.*—Under warm, 25° C., temperature, plants of the cultivar Tenorio will flower after 9 weeks of exposure to controlled photoperiods (short day/long night conditions). Under cooler growing temperatures, 20° C., plants of the cultivar Tenorio will flower after 11 weeks of exposure to controlled photoperiods. First flower open is the terminal flower at the main axis and is followed by the opening of the terminal flowers of the side branches of the inflorescence.

E. *Flower diameter.*—1.6 cm.

F. *Flower buds.*—1. Shape: Oblong becoming tubular with development. 2. Size: a. Length: 12 mm. b. Width: 2 mm.

G. *Petals.*—1. Quantity: 4 united in corolla. 2. Shape: Nearly round. 3. Tip: Cuspidate. 4. Length: 7 mm. 5. Color: a. When opening: 46B. b. Mature, top side: 46A. c. Mature, under side: 34D/37D. d. Fading to: 45B.

H. *Peduncle.*—1. Length: 5 mm. 2. Color: 138A.

I. *Reproductive organs.*—1. Stamens: a. Staman number: 8. b. Anther shape: Flat, elliptic. c. Filament color: Yellow. d. Pollen color: Yellow. 2. Pistils: a. Stigma shape: Flat. b. Stigma appearance: Crystalline. c. Style color: Greenish white. d. Ovary number: 4-celled. e. Ovary size: (1) Length: 6 mm. (2) Width: 1 mm. f. Ovary color: Green.

Disease resistance: No known Kalanchoe diseases observed to date.

Seed production: Seed production has not been observed.

It is claimed:

1. A new and distinct cultivar of Kalanchoe plant named Tenorio, as illustrated and described.

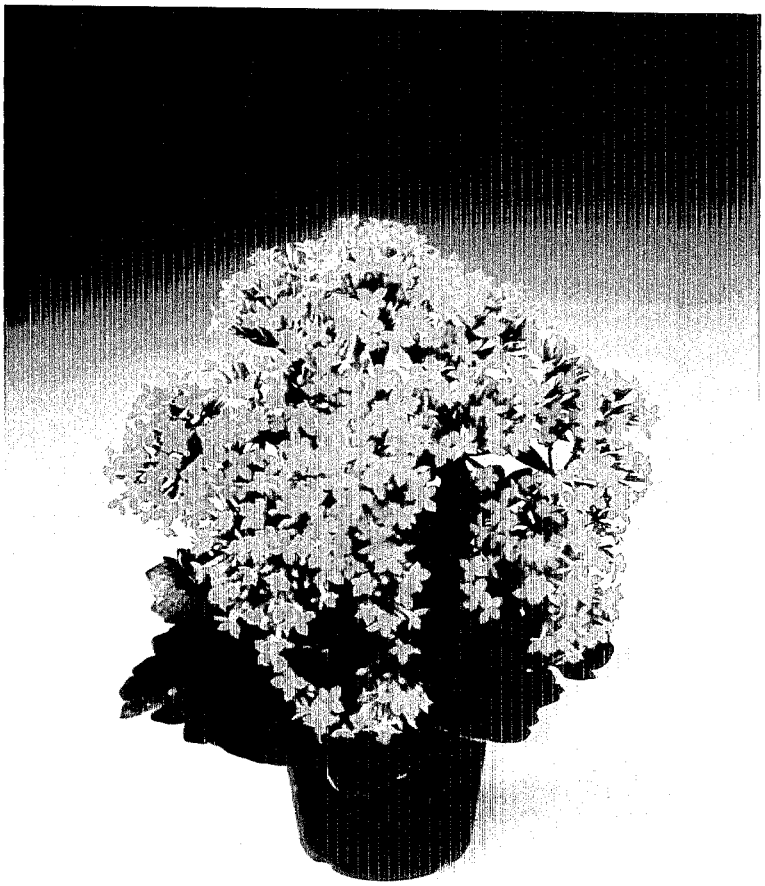

* * * * *